Figure 1:
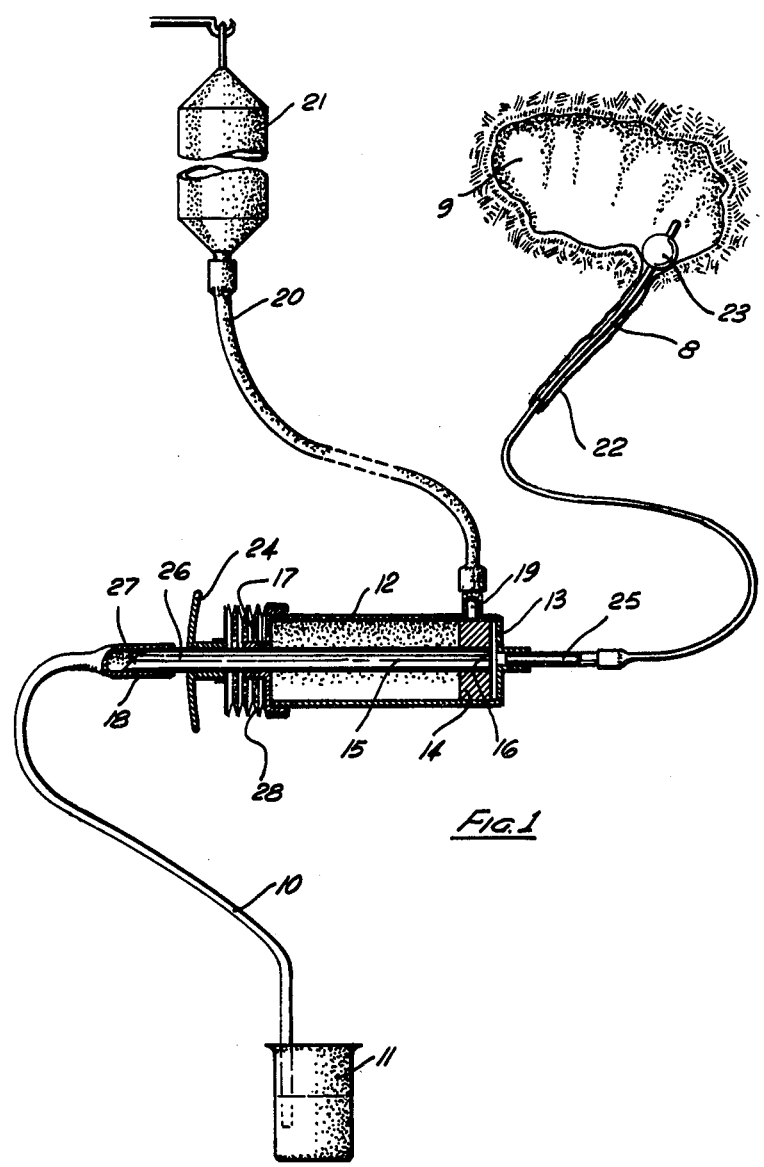

United States Patent [19]

Wilson

[11] Patent Number: 4,457,755
[45] Date of Patent: Jul. 3, 1984

[54] SURGICAL 'IN-LINE' EVACUATOR

[76] Inventor: John D. Wilson, 29 Woolwich Rd., Hunters Hill, N.S.W. 2110, Australia

[21] Appl. No.: 359,419

[22] Filed: Mar. 18, 1982

[30] Foreign Application Priority Data

Apr. 2, 1981 [AU] Australia ............................ PE8270

[51] Int. Cl.³ .............................................. A61D 7/00
[52] U.S. Cl. .................................... 604/184; 604/7/38
[58] Field of Search ........................ 604/30–36, 604/38, 54, 73, 74, 93, 128, 152, 171, 181, 183, 184, 186, 192, 203, 231, 218; 128/765, 766

[56] References Cited

U.S. PATENT DOCUMENTS 1,410,530  3/1922  Larche ..................................... 604/7
2,923,296  2/1960  Adams et al. .............. 128/DIG. 24
3,703,899  11/1972 Calinog ............................... 604/170

FOREIGN PATENT DOCUMENTS 262824  4/1965  Netherlands .......................... 604/49

Primary Examiner—C. Fred Rosenbaum
Assistant Examiner—Sherri E. Vinyard
Attorney, Agent, or Firm—Peter L. Berger

[57] ABSTRACT

A surgical evacuator or catheter for drawing fluids from a patient, or injecting irrigation liquid into the patient, includes a proximal portion, a distal or drainage portion and an irrigation liquid inlet all of which open to the proximal end of a cylinder. The cylinder contains a piston or plunger by way of which said drainage portion opens to the cylinder. The proximal portion, the drainage portion and the liquid inlet are individually capable of closure to prevent liquid flow therethrough.

5 Claims, 7 Drawing Figures

SURGICAL 'IN-LINE' EVACUATOR

In the surgical treatment of patients (whether human or animal) it is frequently necessary to evacuate detrimental fluid accumulates from a cavity or sac in the patient's body. The cavity or sac may be a wound (caused by surgery or otherwise) which has been closed at its outermost region by suturation yet is required to heal from its innermost region in the direction towards the outermost region, or it may be a natural sac such as the bladder, a lung, the stomach or the like.

In many cases nothing more than a simple drainage tube, duct or catheter is required, but in others the fluid to be drained may contain blood clots, mucus, or other matter less fluent than the remainder of the accumulate. When this is so, the intake end of an ordinary drainage tube will frequently become occluded by the less fluent matter and it then becomes necessary to apply a substantially greater suction to the drainage tube in order to induce the obstructing matter to enter the tube and proceed to waste by way thereof; moreover, to facilitate evacuation, it is often desirable to irrigate the cavity or sac to be drained, with a saline or other solution to act as vehicle for the matters to be evacuated.

Although the invention is applicable to a variety of drainage uses as indicated above, the need for an effective in-line evacuator arose in connection with the removal of blood clots from the bladder following prostatic or other surgery related to urological disorders. Because of this, the invention is described herein largely in terms of a urological in-line evacuator.

In the prior art, it has been common to use what is known as the cystoflo drainage system. This prior system comprises a catheter whereof the proximal end portion is entered into the bladder and the distal end portion opens to a urinary drainage bag or other receiver for the drained matter. The catheter of such a system includes a compressible rubber bulb which can be stocked with an irrigating liquid and delivered into the bladder by compression of the bulb. For suctional purposes, pressure on the bulb is relaxed so that of its own elasticity, the bulb tends to resume its unsqueezed globular shape. Experience has shown that the prior system just discussed fails to develop a sufficiently strong suctional effect and frequently becomes quite ineffective in the presence of heavy bleeding involving extensive clotting. When that happens, it is necessary to break the closed in-line system, thereby risking loss of its necessary sterility, and endeavour to evacuate the clots by use of other means. Even if this endeavour is successful it still involves another risk of sterility loss in re-establishing the broken in-line system.

The object of the present invention is to overcome the indicated shortcomings in the provision of an in-line evacuator which:

(1) provides a more-effectively powerful evacuation suction;
(2) will avoid the necessity, to break the closed and sterile in-line system and thus reduce the likelihood of introducing infection; and
(3) will remove need for catheter irrigation trays which are costly to set up and not always readily available when needed urgently.

The invention provides a surgical in-line evacuator comprising:

(a) a duct tube having a proximal end portion adapted to be introduced into a bodily cavity or sac to be drained and a distal end portion leading to waste;
(b) a cylindrical chamber to one end of which said proximal end portion is open;
(c) an axially holed piston plunger reciprocable longitudinally of said chamber;
(d) a tubular piston rod, upon one end of which said piston plunger is mounted, so that the bore of said piston rod opens to that end of said chamber to which said proximal end portion is open, and whereof the other end is open to said distal end portion;
(e) an irrigation liquid inlet opening to said chamber adjacent the proximal end of said chamber, and
(f) fluid-flow control means associated with each said proximal end portion, said distal end portion and said liquid inlet.

An example of the invention is shown in the drawings herewith:

FIG. 1 of the drawings is purely diagrammatic representation of a urological in-line evacuator according hereto.

FIGS. 2 to 7 are schematic representations of a cylinder and plunger arrangement (already shown in FIG. 1) showing the parts thereof disposed in accordance with several stages in usage.

Referring to the drawings, a duct tube has a proximal end portion 8 adapted to be introduced into the bladder indicated at 9. The proximal end portion of the duct tube may conveniently be in one or more separable parts as will be understood. The duct tube has a distal end portion 10 from which evacuated liquid may be discharged in any convenient manner, for example, by being sent into a common urinary drainage receptacle 11. A cylindrical chamber 12 is connected in line with duct portions 8 and 10, the chamber having one end 13 open to proximal end portion 8 and housing a piston plunger 14 which is reciprocable longitudinally of chamber 12. Plunger 14 is mounted on a tubular piston rod 15, the arrangement being such that the piston rod 15 has one end 16 open to that end of chamber 12 in communication with proximal duct tube 8. The piston rod 15 slides in a bearing 17 and has its other or distal end 18 open to distal end portion 10. An irrigation inlet 19 opens to chamber 12 and is connected by supply tube 20 with a source of irrigation liquid indicated at 21.

That portion of the proximal end 8 which is inserted into the bladder 9 by way of the urethra 22 may be of the common type known as a "Foley" balloon catheter as indicated as 23.

Figure 2:
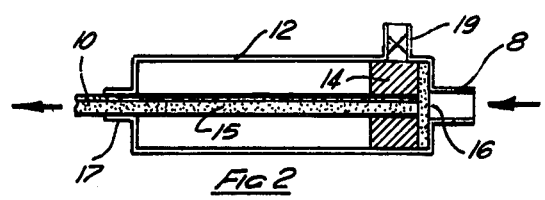

When the evacuator is required to be used in the manner of a simple drainage tube, the piston plunger 14 is located as shown in FIG. 2 so that it closes irrigation inlet 19. This inlet could be closed by furnishing it with an on-off cock, but closure by way of plunger 14 is preferred since the apparatus is thus less complicated.

The evacuator, (as shown in FIG. 2) operates in simple drainage fashion like an ordinary catheter.

Figure 3:
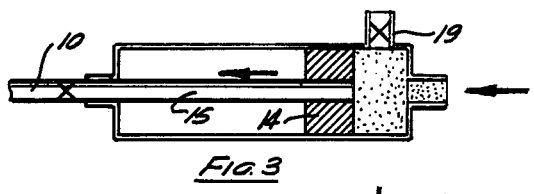
Figure 4:
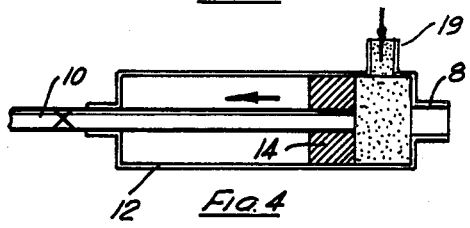

In some cases it may be required to increase suctional force on portion 8 without irrigation being immediately necessary. If so, passages 19 and 10 are closed, and plunger 14 retracted as indicated in FIG. 3. This retraction is effected by finger pull on handpiece 24 (FIG. 1) fixed on piston rod 15.

As previously indicated, passages such as 19, and also those at 25 and 26, are each provided with closure means, and these means may be hand operated on-off cocks. However such cocks are not preferred since there is a risk that they may be inadvertently left in "off" or closed position when not required; moreover, such cocks add unnecessary complication in the apparatus as a whole. For preference, each of the tubes 8, 10 and 20 is made of rubber, plastics or like flexible material so that the passage, or passages, concerned may be closed simply by hand or finger pressure sufficient to bend the tube or tubes to be closed so as to halt fluid flow through it or them. This has the advantage that when any one of the passages 8, 10 or 20 is required to revert to open position, it will do so of its own accord (due to the resilience of the material from which it is made) immediately following relaxation of the hand or finger pressure which caused it to fold into closed position.

In the case of passage 19, it is effectively closed by plunger 14 when that plunger is in a position to do so as shown in FIG. 2. When the plunger is not in that position, passage 19 may be closed (as shown in FIGS. 3, 5, 6 and 7) by tube folding effected by way of the user's thumb pressure.

This application of manual pressure may be facilitated (particularly in the case of passage 26 which would normally be closed by hand palm pressure while the fingers of the same hand are hooked about handpiece 24) by providing passage (26) with a flat, oblique end 27 against which the adjacent portion of tube 10 can be flatly pressed by the palm.

Figure 5:
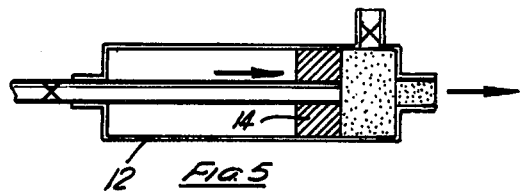

When the bladder 9 is to be irrigated, cylinder 12 (see FIG. 4) is charged by closing passage 10, opening passage 19 and retracting plunger 14. To deliver the charge, passage 10 remains closed, passage 19 is closed, and plunger 14 advanced as shown in FIG. 5.

Figure 6:
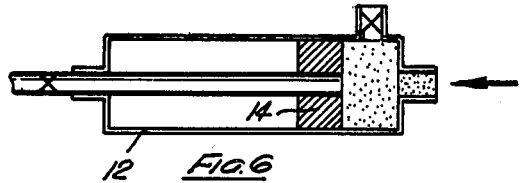
Figure 7:
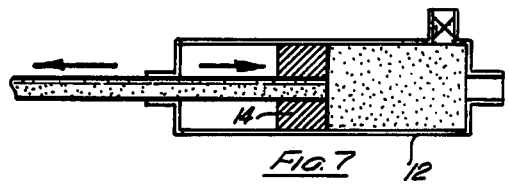

If irrigation is followed by high suction evacuation, as indicated in FIG. 6, the apparatus is conditioned and operated in the same way as explained in FIG. 3. Following such evacuation the contents of cylinder 14 are expelled, as shown in FIG. 7, and the apparatus reverted to ordinary catheter drainage as shown in FIG. 2.

As a further safeguard against loss of internal sterility, the space between bearing 17 and handpiece 24 may be sealed by use of a conventional sylphon or concertina sleeve as indicated at 28 in FIG. 1.

It will be appreciated that further modifications may be applied to the evacuator as described above. For example, the irrigation inlet 19 may be placed in the end 13 of chamber 12 or otherwise as may be convenient provided it is closable (by plunger 14 or otherwise) when required. Again, a compression loading spring may be applied between handpiece 24 and the adjacent end of chamber 12 so that the evacuator may be used as a self-acting wound drain. Such a spring could be incorporated in, or constituted by, a concertina sleeve such as that indicated at 28; or, in the event of such a sleeve not being incorporated, by an ordinary helical spring sleeved on piston rod 15 between the handpiece 24 and the adjacent end cover for chamber 12. If a concertina sleeve such as 28 is required to be employed with a spring as just discussed, the spring may be closely sleeved about rod 15 between bearing 17 and the mounting boss 29 of handpiece 24; that is, inside a sleeve such as 28.

It will be further appreciated that in some cases it may be desirable, for safety or other reasons, to lock the plunger 14 in its closed position (as shown in FIG. 1) so to ensure against unwanted discharge of liquid from container 21. This may be accomplished by use of a common grub screw able to bear upon rod 15 through bearing 17, or by a link pivoted on cylinder 12 and able to engage handpiece 24, or otherwise.

Earlier herein it was stated that end portion 10 may discharge "into a common urinary drainage receptacle". In this connection it will be appreciated that such a receptacle may be constituted by a common urinary drainage bag, being a collapsible flexible bag which is closed except for its communication with drainage outlet 26. Such a closed bag is preferred since, by comparison with an open receptacle, it increases sterility security.

I claim:

1. A surgical in-line evacuator comprising:
   a cylindrical chamber having one end opened and its other end closed,
   a catheter tube having one end connected to said open end of said cylinder chamber and its other end adapted for insertion into a body cavity to be drained,
   an open-ended plunger tube longitudinally slidable through the closed end of said cylindrical chamber so that said plunger tube has an inner end open to the inside of said cylindrical chamber and an outer end disposed outside that cylindrical chamber,
   means for closing said outer end of said plunger tube,
   a piston plunger axially slidable within said cylindrical chamber and mounted on said inner end,
   an irrigation liquid inlet which opens to said cylindrical chamber adjacent said open end of said cylindrical chamber,
   an irrigation liquid supply source tube-connected to said inlet; and
   means for closing said inlet, said means for closing comprises said piston plunger closing said inlet when the plunger is at the end of its stroke adjacent said open end.

2. An evacuator according to claim 1, wherein the means to close said outer end comprises a flat, obliquely disposed seating constituting said outer end and a flexible drainage tube which is connected to said outer end and is depressible to close said seating.

3. An evacuator according to claim 1, wherein said means to close said inlet consists of a flexible tube whereby said irrigation liquid supply source is tube-connected to said inlet.

4. An evacuator according to claim 1, wherein the outer end portion of said plunger tube and an outside portion of said cylindrical chamber are sealed by way of a concertina sealing sleeve.

5. An evacuator according to claim 1, wherein said catheter tube, said plunger tube and said liquid inlet each include a passage portion which opens into said cylindrical chamber, wherein at least one of said passage portions comprises a resilient tubular material amendable to manual distortion to control liquid flow therethrough.

* * * * *